United States Patent [19]

Kildal-Brandt et al.

[11] Patent Number: 5,449,624
[45] Date of Patent: Sep. 12, 1995

[54] WINDOWING IN RATE ASSAYS WITHOUT USING INITIAL PREDICTED CONCENTRATION

[75] Inventors: Paul A. Kildal-Brandt, Webster; Thomas A. Weber, Rochester, both of N.Y.

[73] Assignee: Eastman Kodak Company, Rochester, N.Y.

[21] Appl. No.: 203,081

[22] Filed: Feb. 28, 1994

Related U.S. Application Data

[63] Continuation-in-part of Ser. No. 3,921, Jan. 13, 1993, abandoned.

[51] Int. Cl.⁶ ............................................. G01N 35/00
[52] U.S. Cl. ..................................... 436/500; 436/46; 436/164; 436/169; 436/170; 436/71; 436/513; 422/56; 422/63; 422/64; 422/67
[58] Field of Search ................ 436/46, 164, 169, 170, 436/8, 500, 513, 71; 422/56, 63, 64, 67

[56] References Cited

U.S. PATENT DOCUMENTS

| | | | |
|---|---|---|---|
| 4,225,576 | 9/1980 | Denning et al. | 436/500 |
| 4,368,509 | 1/1983 | Li | 364/148 |
| 4,750,133 | 6/1988 | Eiskamp et al. | 364/497 |
| 4,771,008 | 9/1988 | Miura et al. | 436/500 |
| 4,777,128 | 10/1988 | Lippa | 435/5 |
| 4,907,076 | 3/1990 | Ohsawa | 358/80 |
| 4,959,796 | 9/1990 | Hidaka et al. | 364/497 |
| 5,025,389 | 6/1991 | Imai et al. | 364/497 |
| 5,154,906 | 10/1992 | Dalin et al. | 423/390 |
| 5,232,668 | 8/1993 | Grant et al. | 422/82.05 |
| 5,278,080 | 1/1994 | Midgley et al. | 436/500 |
| 5,342,788 | 8/1994 | Kunst et al. | 436/500 |

*Primary Examiner*—James C. Housel
*Assistant Examiner*—Harold Y. Pyon
*Attorney, Agent, or Firm*—Dana M. Schmidt

[57] ABSTRACT

A method of assaying analytes using a rate procedure is described where the change in density over time has a variable rate. The method features the steps of depositing the sample onto a dried slide-like test element, making an initial rate reading during an early time window, using the initial rate readings in a comparison study with rates from known low and high concentration results to predict whether the sample rate will be sufficiently low as to be ascertainable during a later time window or not, and then calculating a rate of reaction and concentration during either the early time window or the early time window with a portion of the later time window, respectively. To avoid the possibility of a consistent bias, the initial rate readings are used directly in the comparison study without first calculating a concentration, by comparing the initial rate reading of a sample against known rates corresponding to samples with low and high concentrations to determine the length of the time window to be used in the rate calculation.

6 Claims, 8 Drawing Sheets

WINDOWING IN RATE ASSAYS WITHOUT USING INITIAL PREDICTED CONCENTRATION

RELATED APPLICATION

This application is a Continuation-In-Part application of U.S. Ser. No. 003,921, filed on Jan. 13, 1993 now abandoned.

FIELD OF THE INVENTION

The invention relates to an improved method for making reaction rate determination of analytes, such as in a clinical analyzer, particularly those having rapidly changing rates.

BACKGROUND OF THE INVENTION

Figure 1:
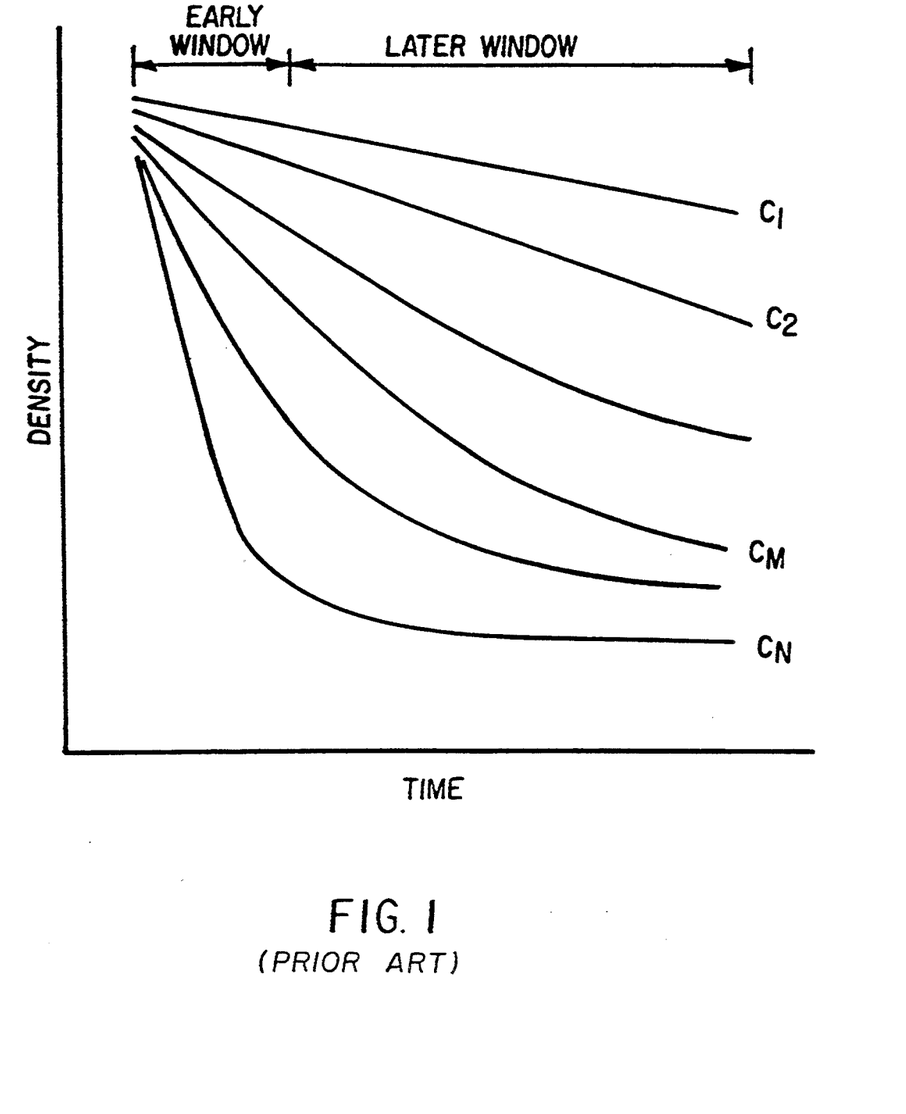
FIG. 1 is a graph that illustrates the problem and the conventional approach thereto.

The desk-top analyzers introduced by Eastman Kodak Company in 1986 under the trademark "Ektachem DTSC" analyzer calculated rate reactions using a screening scheme shown in FIG. 1 of this application, except that during the "early window", not only were the initial rates ascertained, but also the predicted concentrations as a required step. E.g., $DD_s/DT_s$ predicted a concentration of $C_s$. Such predicted concentrations were then checked against a known high concentration $C_m$ (corresponding to the curves shown). If the value of $C_s$ was within the range of $C_1$ through $C_m$, then the analyzer used all the density readings in the early window, along with a portion of the density readings in the later window, to determine the rate for the following reasons:

Low concentration samples tend to have linear curves during the early window as well as a portion of the later window, producing rates which distinguish between sample concentrations $C_1$ through $C_m$. However, in the event the predicted concentration $C_s$ was beyond $C_m$, in other words, too large a concentration, then the analyzer made the "final" rate readings only during the early window. The reason is that concentrations larger than $C_m$ had rates that flattened out so much during the later window that variations on those larger concentrations were indistinguishable from each other and produced rates similar to those found for low concentration samples.

Although that procedure works well with rate reactions conducted on the "DTSC" analyzer, it creates a problem when assaying certain immuno-rate chemistries such as digoxin and phenytoin. The latter have rapid changes in the rate curve which, we have discovered, produces a consistent bias in the results achieved by that method. Therefore, there has been a need prior to this invention to develop an initial screening program that does not suffer from this problem, when applied to these immunorate chemistries.

SUMMARY OF THE INVENTION

We have discovered that the screening scheme described above can not only be achieved by leaving out a required step in the process of the prior art, but also that the scheme is improved, at least when used with the noted immunorate chemistries, by so doing.

More specifically, there is provided by the invention a method of assaying in an analyzer analytes selected from the group consisting of digoxin, phenytoin, phenobarbital and CRP and having a change in density over time that is variable, the method comprising the steps of:

depositing the sample onto a dried slide test element, detecting density readings over time, making an initial rate reading comprising a rate of change of said density readings over time during an early time window, comparing said initial rate reading with only known rates stored in said analyzer and selecting a time window from a plurality of time windows for final rate calculation based solely on the rate comparisons, calculating a final rate from density readings within said selected time window, and then calculating a concentration of said digoxin, phenytoin, phenobarbital or CRP from said final rate calculation, whereby said window-selecting step is performed without first calculating a concentration, and a bias is avoided for said analytes that would occur if the window-selecting step were based upon a comparison with a predicted concentration.

Accordingly, it is an advantageous feature of the invention that a rate assay can be analyzed using an early time window for samples producing high rates and later time window for samples with lower rates, without incurring a bias due to an unusually high change in rate of reaction with time.

It is a related advantageous feature that such an assay can be used without a step heretofore considered necessary, namely the conversion of the measured rate of change to a predictable concentration, prior to comparing that against values for low and high concentration results.

Other advantageous features will become apparent upon reference to the following Detailed Description when read in light of the attached drawings.

DETAILED DESCRIPTION OF THE PREFERRED EMBODIMENTS

The following description is directed to the preferred embodiments, wherein densities are detected using dried slide-like test elements, hereinafter "slide elements", of a preferred type, to assay for preferred analytes using preferred algorithms. In addition, the invention is useful in rate assays that detect absorbance, using reagents in a form other than the preferred slide elements, to assay for other analytes using other algorithms, provided that they skip the step of determining a predictable concentration before comparing the detected rate with a range of values that controls the time window used.

The preferred test elements are dried slide elements available under the trademark "Ektachem" from Eastman Kodak Co., for the assaying of an analyte selected from the group consisting of digoxin, phenytoin, phenobarbital, and CRP. The chemistries for such assays can be understood by reference to, e.g., European Patent Applications 468,590 and 468,591.

Additionally, it has been shown that the invention is also applicable to rate assaying the analytes selected from the group consisting of T4 and carbamazepine, since these also have produced a similar error bias when using the prior art "SDW algorithm" discussed hereinafter.

Still further, it is contemplated that the following assays can also be used with this invention to determine them as rate assays, because they use the same color-producing chemistry and have similar rate curves: Those selected from the group consisting of Thyroid Uptake, Valproic Acid, Gentamicin, Tobramycin, Vancomicin, Primidone, Procainamide, N-acetyl Procainamide, Theophylline, Apo lipoproteins A and B, hCG, CKMB, Troponin, Myoglobin, IgE, IgM, and IgA.

The above-stated "Background" explains the conventional approach that requires the conversion of the rate detected during the "early window", into a predicted concentration. More specifically, that process used an algorithm known as the "SDW algorithm".

That algorithm is as follows, where the following terms have the noted meanings:
N=the minimum number of points in the time window;
M=the maximum number of points in the time window;
AAR=the algorithm analyzer range (i.e. high concentration);
W=window modulator (usually equal to 1);
TIND=induction time (in minutes), which identifies the start of the early window.

The procedure is as follows:
(1) calculate an initial rate (InitRate) using the first N density readings following TIND;
   the rate is calculated by linearly regressing the density readings against the read times;
(2) predict an initial concentration (InitConc);
(3) calculate the ratio R where:

$$R = \frac{InitConc}{AAR}$$

when predicting a sample; except that
  (a) if R>1, then set R=1;
  (b) if R<0, then set R=0;
(4) determine the number of density readings in the final time window (PTS):

$$PTS = M - [R^W \cdot (M-N)]$$

(5) calculate the final rate (FinalRate) using PTS density readings following TIND;
(6) if predicting, convert the FinalRate to a final predicted concentration.

In that algorithm, it is apparent that step 2 requires conversion to a predicted concentration before the time window is determined using steps (3) and (4).

A brief example showing the execution of the algorithm follows:
Assume the parameters of the SDW algorithm are:
N=6
M=24
AAR=300
W=1
TIND=2
(In this example, density increases with time instead of decreases, in contrast to the example of FIG. 1, due to the chemistries used.)

Figure 2:
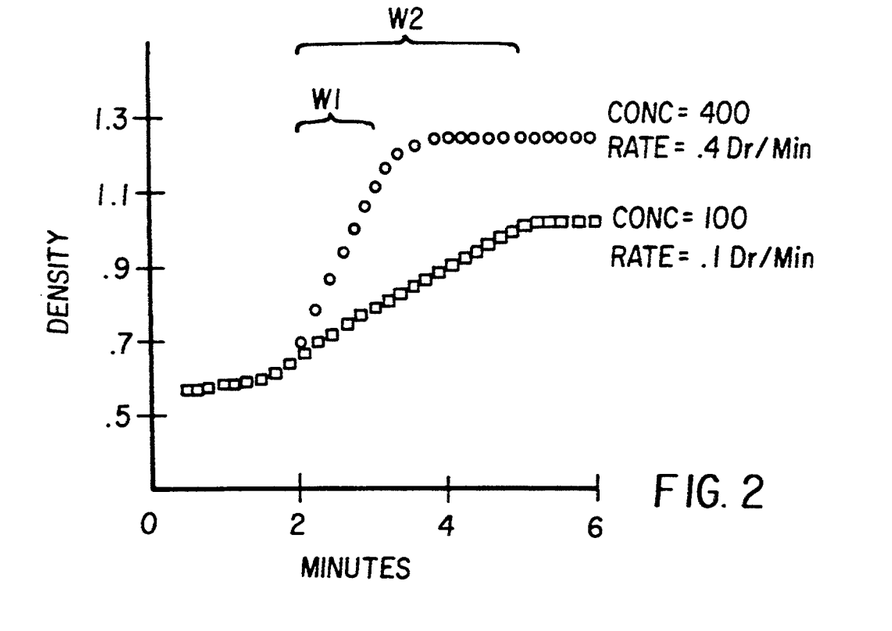
FIG. 2 is a plot of kinetic curves used as an example.
Figure 3:
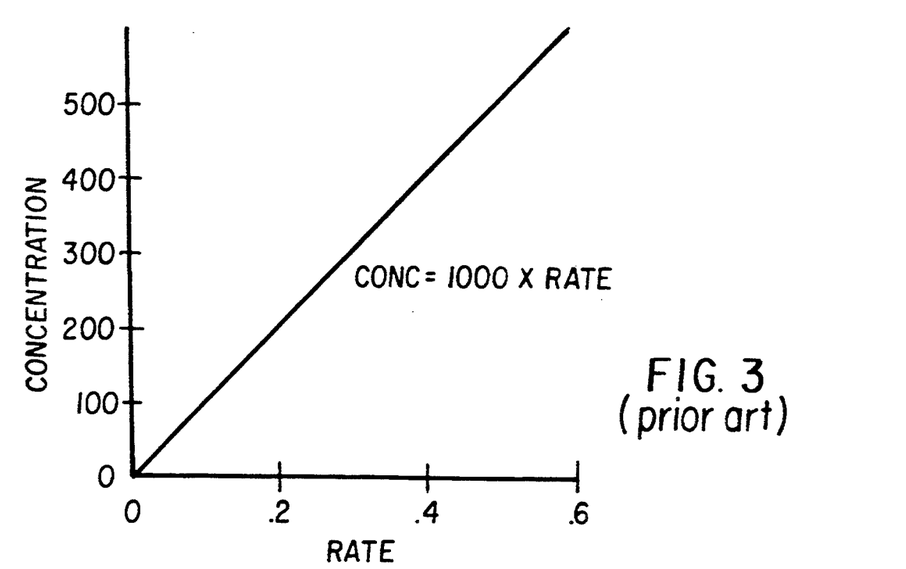
FIG. 3 is a calibration curve that can be calculated from the data of FIG. 2 using the prior art procedure.

Kinetic curves for a low and high sample are plotted in FIG. 2. Since the TIND is 2 and N is 6, the initial time window, denoted as W1, is [2, 3] minutes. Using the six densities falling in the window W1, the initial calculated rates, InitRate, are 0.1 and 0.4 for the low and high samples respectively. FIG. 3 shows the relationship between concentration and rate for the assay. Rates of 0.1 and 0.4 translate into initial concentrations, InitConc, of 100 and 400 respectively. Executing step (3) produces R values of $\frac{1}{3}$ and 1 for the low and high samples respectively. From step (4), the number of points in the final time window, PTS, is 18 for the low sample and 6 for the high sample.

$$18 = 24 - [(\tfrac{1}{3})^1 \cdot (24-6)]$$

The low sample's final rate, FinalRate, is calculated using the time window [2, 5] minutes denoted as W2 in FIG. 2. The final time window for the high sample is W1 since W1 contains 6 points. The final rates are 0.1 and 0.4 and produce predicted concentration of 100 and 400 for the low and high sample.

Since the kinetic curves of assays run on conventional analyzers such as that available from Eastman Kodak under the trademark "Ektachem DTSC" are linear within the initial time windows, the initial rate estimates are unbiased (i.e., on average one gets the correct rate) for low and high samples. The longer time windows for low concentration samples allow for more density readings in the linear regression and result in better precision.

THE INVENTION

In accordance with the invention, the determination of which time window to use is determined by leaving out the previously required step of predicting an "initial concentration" for purposes of comparing with a range of acceptable values. A preferred algorithm (hereinafter the "VET" algorithm) for doing this is as follows, where the following terms are used:
NL=the minimum time window length (in minutes);
ML=the maximum time window length (in minutes);
HighRate=a high rate for the assay;
LowRate=a low rate for the assay;
W=window modulator defined hereinafter (usually equal to 1);
TIND=induction time (in minutes);
(These are all predetermined values for a particular assay.)

Thus,
(1) calculate an initial rate (InitRate) using the time window [TIND, TIND+NL];
   the rate is calculated by linearly regressing the density readings against the read times;
(2) calculate the ratio R where: (A)

$$R = \frac{\text{InitRate} - \text{LowRate}}{\text{HighRate} - \text{LowRate}},$$

except that:
(a) if R>1, then set R=1;
(b) if R<0, then set R=0;
(3) determine the length of the final time window by evaluating the following equation:

(B) $FWL = ML - [R^W \cdot (ML - NL)]$ (4) calculate the final rate (FinalRate) using the time window [TIND, TIND+FWL];
(5) convert the FinalRate to a final predicted concentration.

Parameter W

The parameter W is known as the window modulator and can be defined as follows:
W is a positive integer which dictates the relationship between the final time window length and the initial rate. The larger the value of w, the larger the final time window will be for any fixed initial rate.

Figure 8:
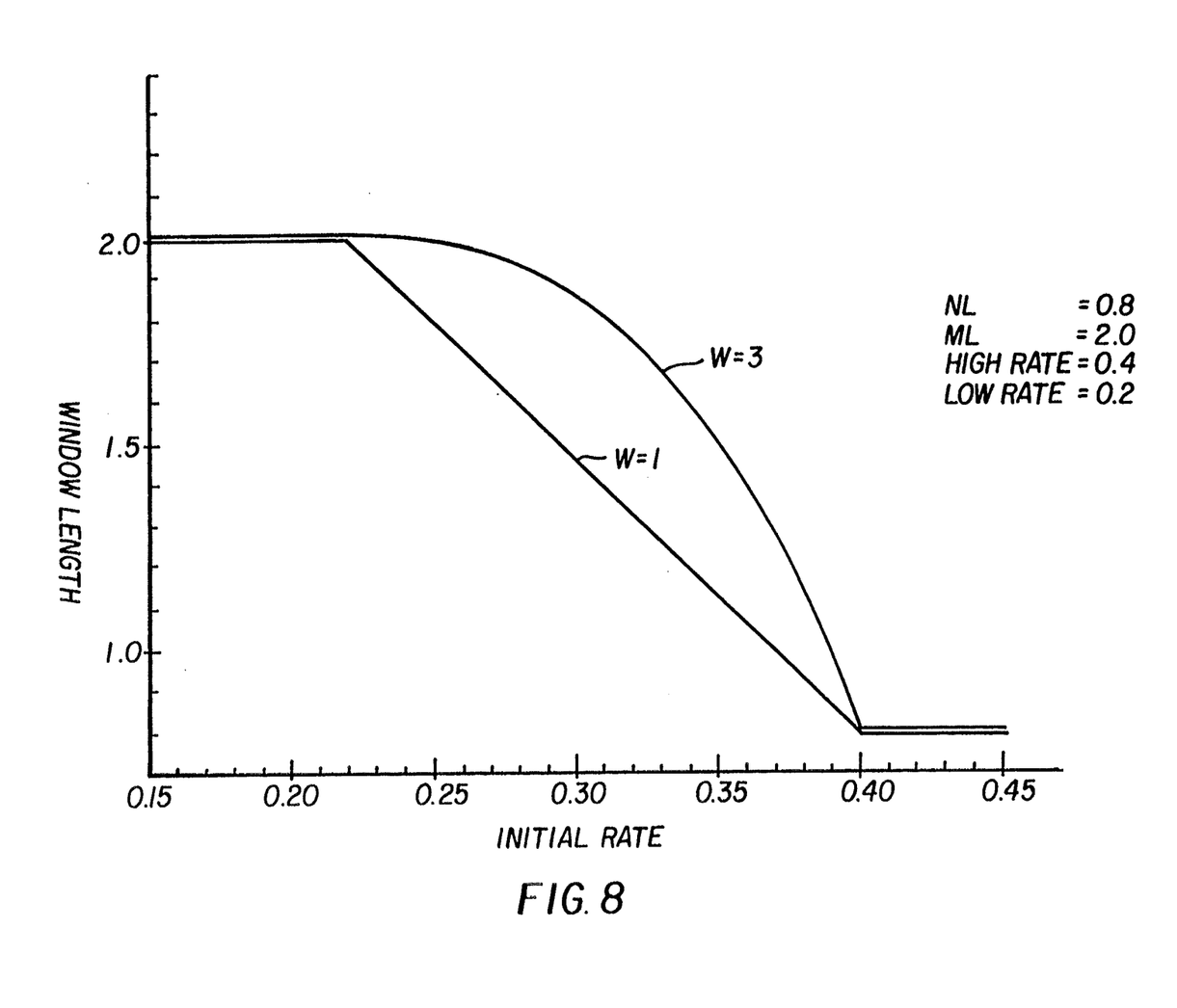
FIG. 8 is a plot of final window length versus the initial rate reading.

In FIG. 8, the effect of the change in value for W is illustrated, for W=1 and W=3 when the other VET parameters are defined as in Table 1:

TABLE 1

| | |
|---|---|
| NL = | 0.8 |
| ML = | 2.0 |
| HighRate = | 0.4 |
| LowRate = | 0.2 |
| TIND = | 0 |

Note that the W=3 curve is always greater than or equal to the W=1 curve. The use of W=3 is demonstrated in Example 2 below.

Like the SDW algorithm, the VET algorithm allows for variable time windows dependent upon the relative concentration of the sample being tested. The VET algorithm solves the consistent bias problem encountered with the SDW algorithm when applied to immuno-rate chemistries by determining the time window in the rate domain rather than the concentration domain.

Whatever algorithm is preferred, conventional programming of the analyzer is used to allow the algorithm to function.

Detailed examples of the improvement follow.

DETAILED EXAMPLES

Example 1 for Digoxin

Kinetic data were collected for nine digoxin samples with known reference values spanning the concentrations 0–6 ng/mL. Nine repetitions of each sample were run for a total of 81 samples in the test, using slides of the type described in European Patent Applications 468,590 and 468,591 for Digoxin. All results have been averaged within a sample. For each repetition, reflectance density readings were taken on an immunorate-capable Ektachem analyzer, such as the analyzer available from Eastman Kodak Company under the trademark "Ektachem 250", every 6 seconds following the application of a wash fluid, and the readings continued for 6 minutes for a total of 60 readings. The data was analyzed using both the SDW and the VET algorithms. In each case, the rate to concentration conversion was defined by calibrating with the sample data. The sample data was then predicted as unknowns and the predictions were compared to the known digoxin concentrations.

For digoxin, high rates correspond to low concentrations. In all the rate assays on the "Ektachem DTSC" analyzer, high rates correspond to high concentrations. This fact requires that N≧M when applying the SDW algorithm to immuno-rate chemistries.

The data was then first evaluated using the "SDW" prior art algorithm, as a control. For this, the parameters were defined as follows:
N=20
M=5
AAR=6.25
W=1
TIND=0

The SDW and VET algorithm parameters were selected in such a way that:
(1) both algorithms would produce similar time windows for each sample, and
(2) low and high samples would use different length time windows.

SDW Calibration

The fluid identification, reference concentrations, and the final calculated rate obtained during calibration are provided in Table 2. During calibration, the SDW algorithm used the reference concentration when determining the final time window.

TABLE 2

| Fluid ID | Ref Conc | Final Rate |
|---|---|---|
| 9 | 5.40 | 0.11716 |
| 8 | 4.83 | 0.12340 |
| 1 | 0.05 | 0.40572 |
| 3 | 0.61 | 0.34179 |
| 7 | 3.43 | 0.16175 |
| 2 | 0.14 | 0.38364 |
| 4 | 1.10 | 0.29305 |
| 5 | 1.50 | 0.25813 |
| 6 | 2.30 | 0.20155 |

Figure 4:
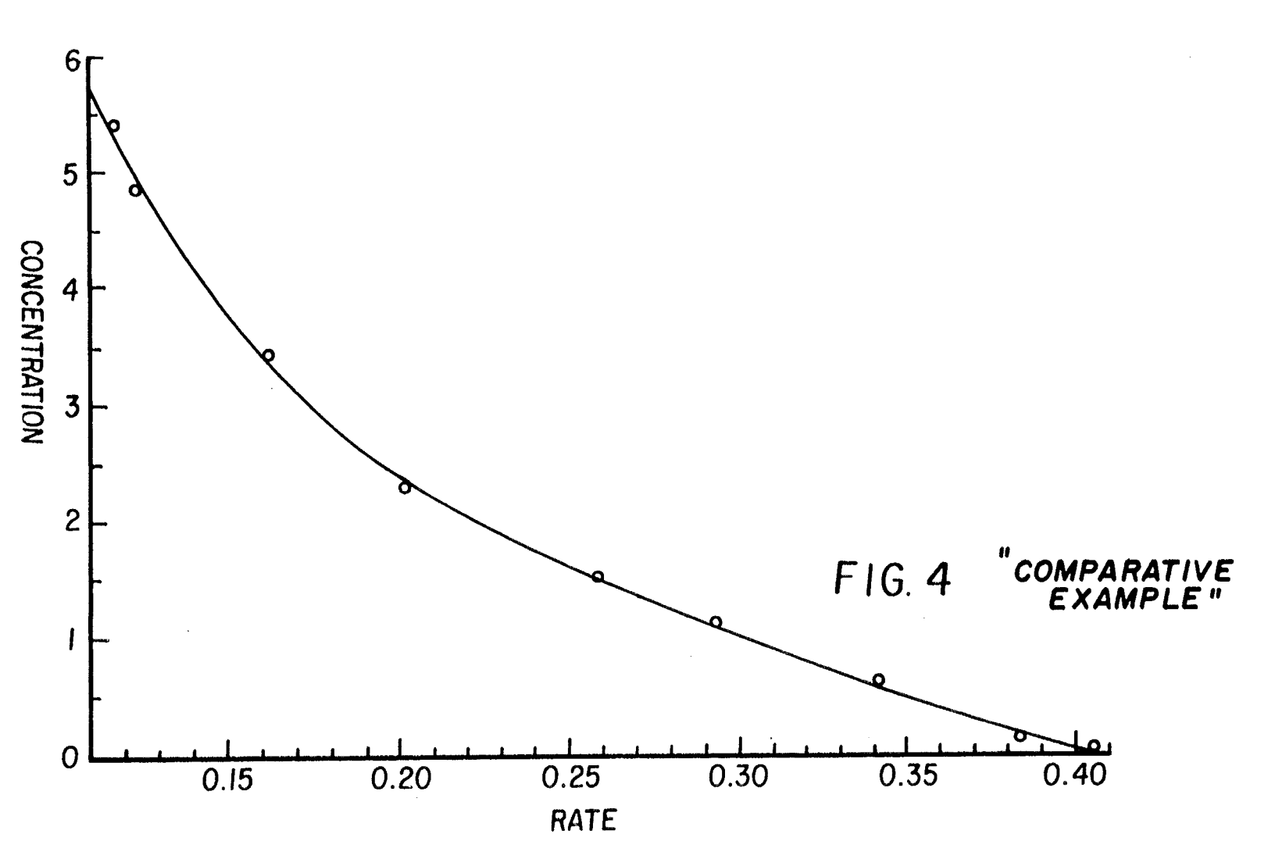
FIG. 4 is a prior art calibration curve similar to that of FIG. 3, except that it is done for a digoxin assay.

The data in Table 2 was used to determine the rate to concentration relationship for this digoxin data and the SDW algorithm. (All concentrations in this and all other Tables are in ng/mL.) The calibration curve is plotted in FIG. 4 and is represented by the following cubic spline, such splines being conventional:

TABLE 3

| SDW Calibration Curve Represented as a Cubic Spline | | |
|---|---|---|
| X | F(X) | F''(X) |
| 0.05 | 9.7722 | 0 |
| 0.13 | 4.6315 | 584.3995 |
| 0.24 | 1.7407 | 52.7518 |
| 0.45 | −0.3464 | 0 |

The digoxin data was predicted using the SDW algorithm and calibration information and the results are provided in Table 4.

TABLE 4

| Fluid ID | Ref Conc | InitRate | InitConc | FinalRate | FinalConc |
|---|---|---|---|---|---|
| 9 | 5.40 | 0.14558 | 3.94 | 0.12583 | 4.84 |
| 8 | 4.83 | 0.14995 | 3.77 | 0.13063 | 4.61 |
| 1 | 0.05 | 0.40571 | 0.02 | 0.40572 | 0.02 |
| 3 | 0.61 | 0.34908 | 0.51 | 0.34179 | 0.58 |
| 7 | 3.43 | 0.18584 | 2.68 | 0.16684 | 3.20 |
| 2 | 0.14 | 0.38364 | 0.20 | 0.38076 | 0.23 |
| 4 | 1.10 | 0.31325 | 0.87 | 0.30066 | 1.00 |

TABLE 4-continued

| Fluid ID | Ref Conc | InitRate | InitConc | FinalRate | FinalConc |
|---|---|---|---|---|---|
| 5 | 1.50 | 0.28080 | 1.23 | 0.26470 | 1.42 |
| 6 | 2.30 | 0.22538 | 1.95 | 0.20834 | 2.23 |

Figure 5:
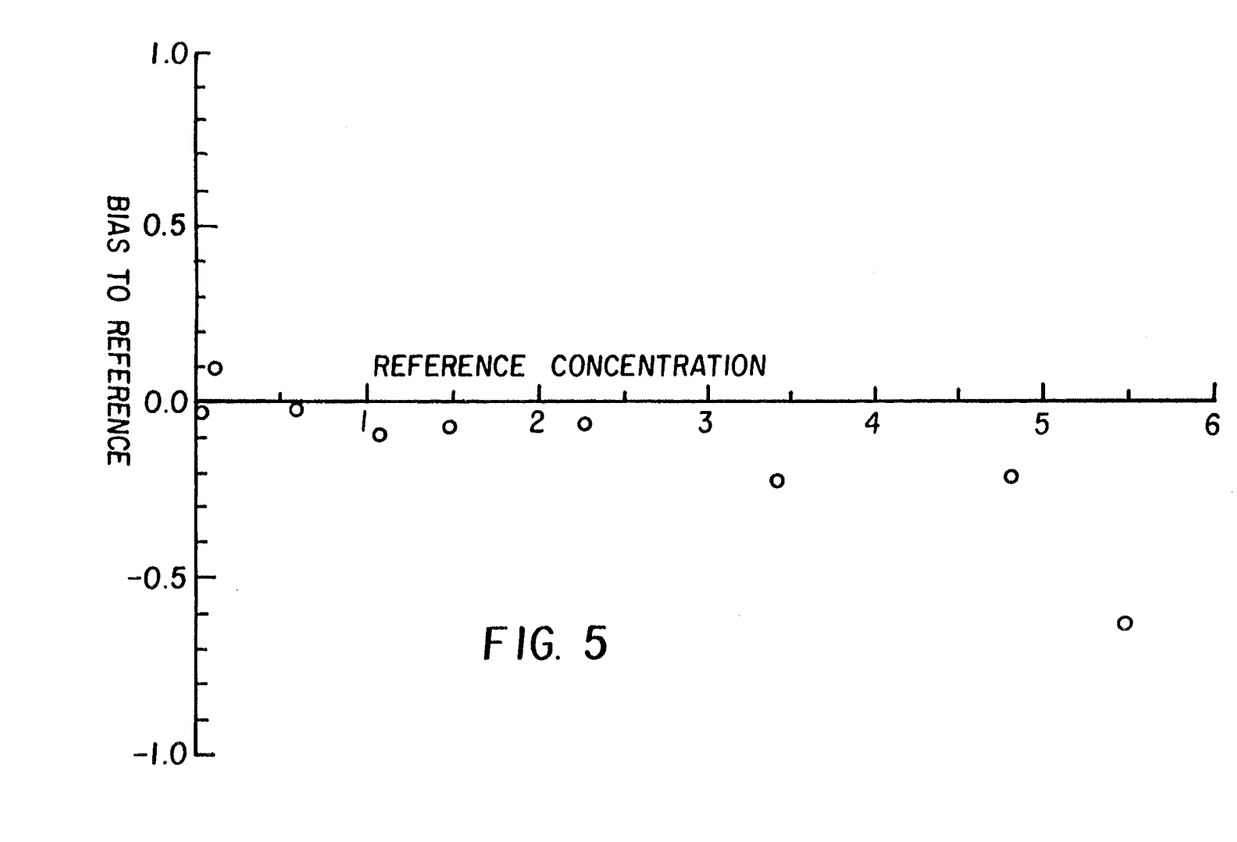
FIG. 5 is a plot of bias resulting from the use of FIG. 4.

The nonlinear digoxin kinetics produce an initial rate which is biased high to the final rate found for the samples during calibration. Converting these initial rates into concentrations using the calibration curve results in initial concentrations which are lower than the reference values. The calculated final time window is too short resulting in a positively biased final rate compared with the rate found during calibration, and a negatively biased final concentration. FIG. 5 is a plot of the fixed negative bias to reference which was produced by the SDW algorithm. As concentration increases, the bias unacceptably deviates in increasing amounts from the zero line.

The same test data was then run through the "VET" algorithm, using the parameters NL=0.5
ML=2.0
HighRate=0.4
LowRate=0.1
W=1
TIND=0

Thus equation (B) becomes $FWL = 2 - [R \cdot (2 - 0.5)]$.

The fluid identification, reference concentrations, and the final calculated rate obtained during calibration are provided in Table 5.

TABLE 5

| Fluid ID | Ref Conc | FinalRate |
|---|---|---|
| 9 | 5.40 | 0.11869 |
| 8 | 4.83 | 0.12340 |
| 1 | 0.05 | 0.40572 |
| 3 | 0.61 | 0.33321 |
| 7 | 3.43 | 0.15393 |
| 2 | 0.14 | 0.38084 |
| 4 | 1.10 | 0.28522 |
| 5 | 1.50 | 0.24725 |
| 6 | 2.30 | 0.18988 |

Figure 6:
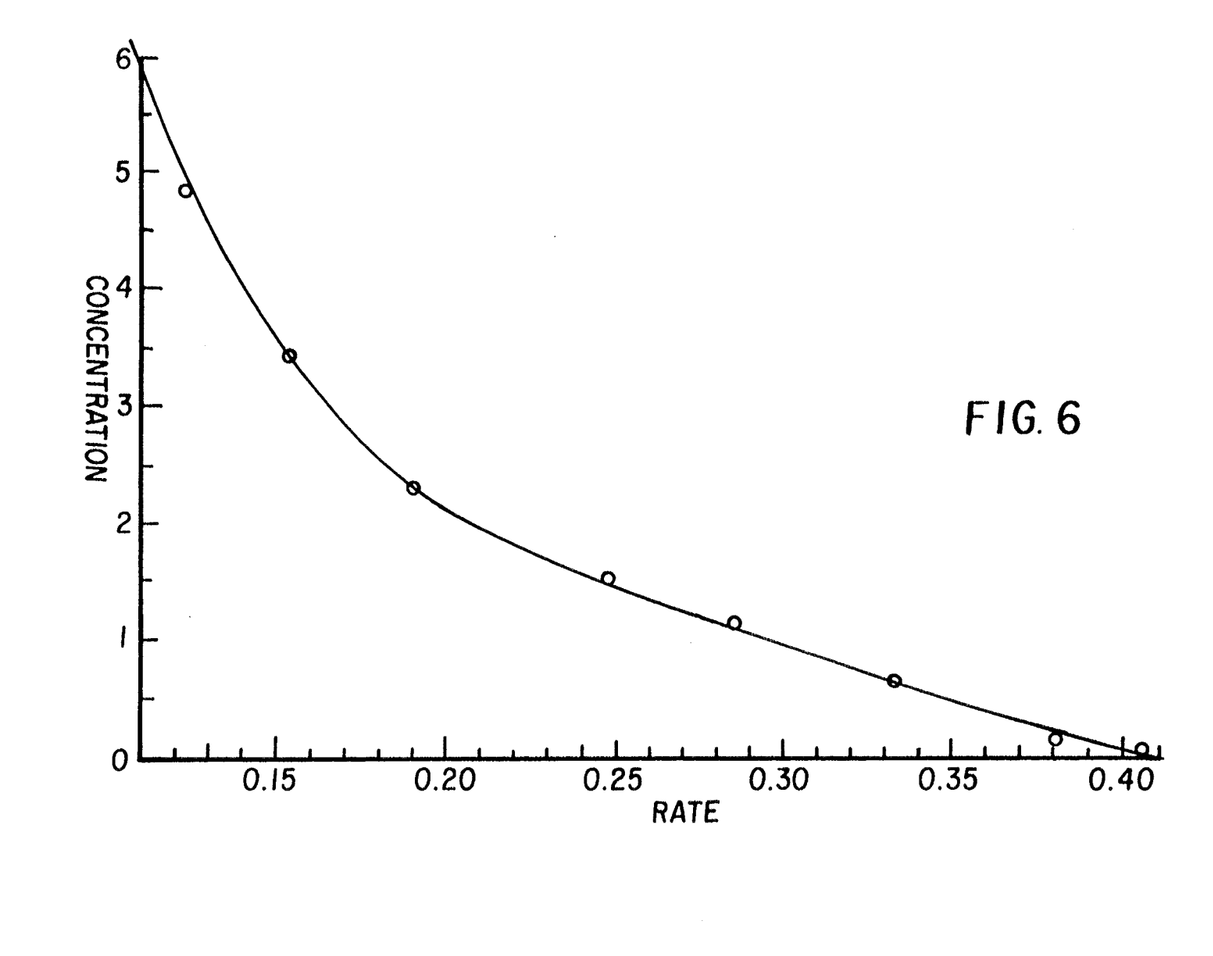
FIG. 6 is a calibration curve similar to that of FIG. 4, using however the procedure of the invention instead of the prior art.

The data in Table 5 was then used to determine the rate to concentration relationship for this digoxin data and the VET algorithm. The calibration curve is plotted in FIG. 6 and is represented by the following ( conventional ) cubic spline:

TABLE 6

| VET Calibration Curve Represented as a Cubic Spline | | |
|---|---|---|
| X | F(X) | F" (X) |
| 0.05 | 10.9824 | 0 |
| 0.13 | 4.5732 | 824.6153 |
| 0.24 | 1.5630 | 28.5228 |
| 0.45 | −0.3701 | 0 |

From this, the digoxin data was predicted using the VET algorithm and calibration information and the results are provided in Table 7.

TABLE 7

| Fluid ID | Ref Conc | InitRate | FinalRate | FinalConc |
|---|---|---|---|---|
| 9 | 5.40 | 0.14558 | 0.11869 | 5.28 |
| 8 | 4.83 | 0.14995 | 0.12340 | 4.98 |
| 1 | 0.05 | 0.40571 | 0.40572 | 0.0 |
| 3 | 0.61 | 0.34908 | 0.33321 | 0.62 |
| 7 | 3.43 | 0.18584 | 0.15393 | 3.41 |
| 2 | 0.14 | 0.38364 | 0.38084 | 0.21 |

TABLE 7-continued

| Fluid ID | Ref Conc | InitRate | FinalRate | FinalConc |
|---|---|---|---|---|
| 4 | 1.10 | 0.31325 | 0.28522 | 1.08 |
| 5 | 1.50 | 0.28080 | 0.24725 | 1.48 |
| 6 | 2.30 | 0.22538 | 0.18988 | 2.32 |

Figure 7:
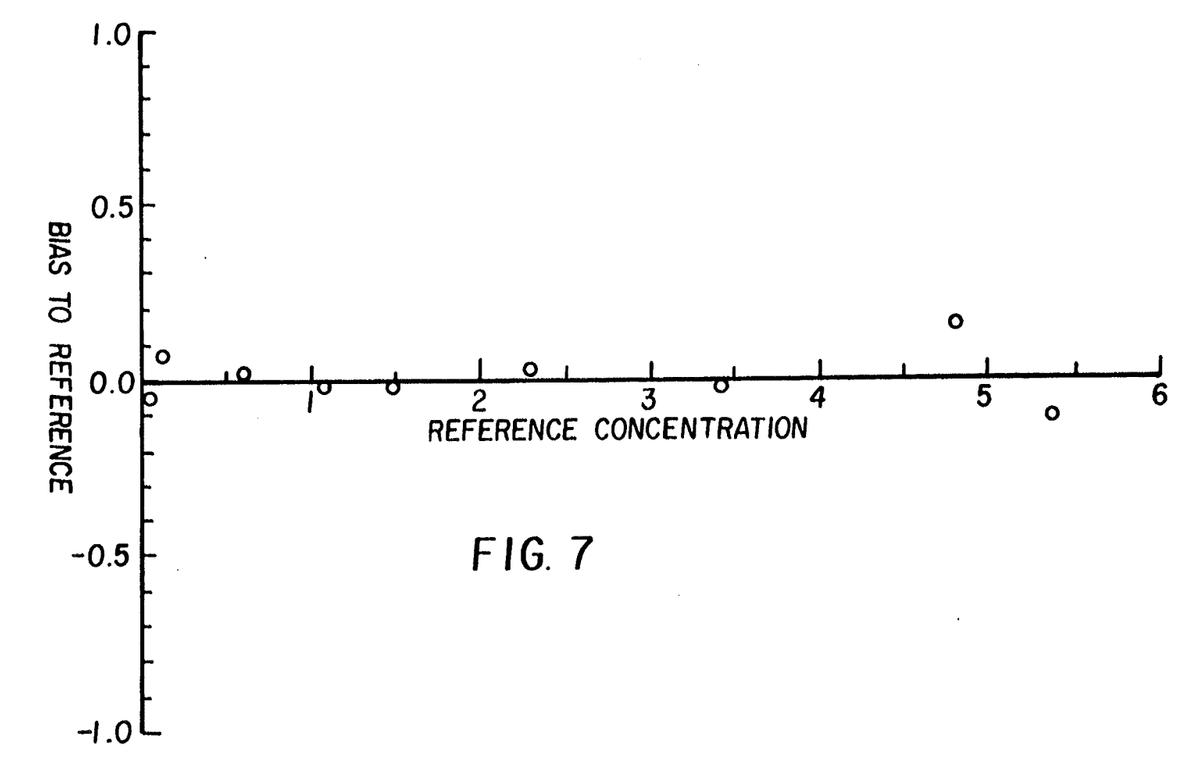
FIG. 7 is a plot of the bias resulting from the use of FIG. 6.

Since the VET algorithm calculates the final time window using only rate information, the same final window is found for the samples in prediction mode and calibration mode. Thus, there is no fixed bias to reference using the VET algorithm. FIG. 7 is a plot of the bias to reference which was produced by the VET algorithm. (The maximum bias shown of +0.15 at 5 ng/mL is a random bias within acceptable limits.)

Example 2 for CRP

The procedure carried out in Example 1 was repeated, except that CRP was the analyte assayed, and the procedure was carried out as follows:

Kinetic data was collected for 69 CRP samples with known reference values spanning the concentration range of 0–160 mg/L. For each sample, reflectance density readings were taken approximately every 7 seconds for 2.7 minutes for a total of 23 readings. The data was analyzed using the VET algorithm with the parameters defined as follows:

TABLE 8

| NL = | 0.8 |
|---|---|
| ML = | 2.0 |
| HighRate = | 0.4 |
| LowRate = | 0.2 |
| W = | 3 |
| TIND = | 0 |

Figure 9:
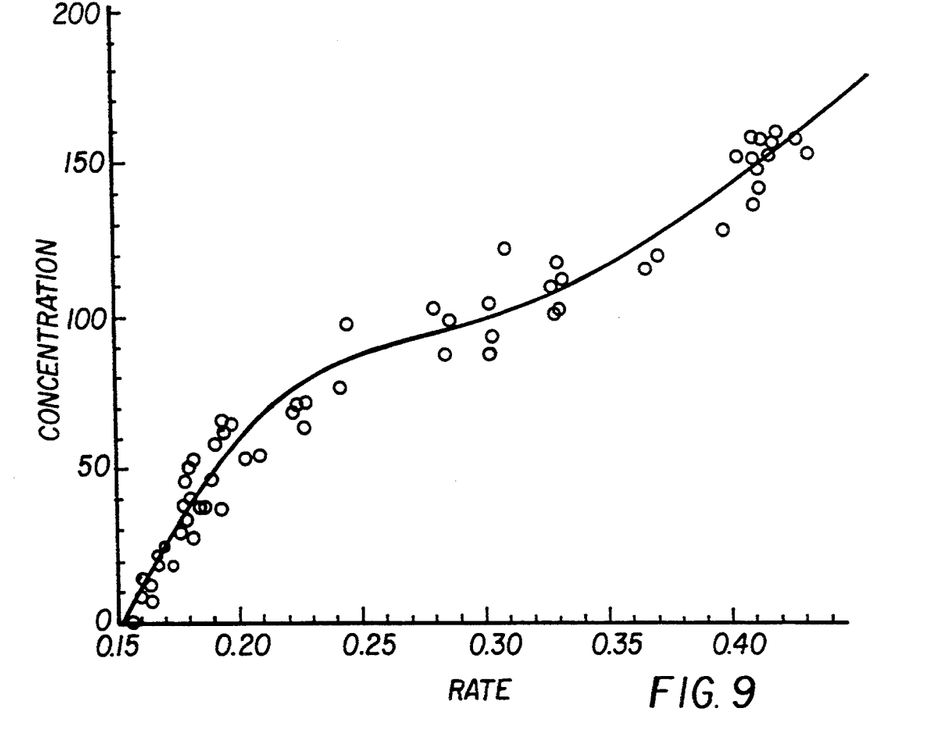
FIG. 9 is a calibration curve of concentration versus rate.

The reference concentration of the samples is provided in Table 9 below, along with calculated information about each sample. The calibration curve used to convert the final rate to a concentration is plotted in FIG. 9 along with the samples. The curve of FIG. 9 can be represented as the following cubic spline:

| CRP Calibration Curve Represented as a Cubic Spline | | |
|---|---|---|
| X | F(X) | F" (X) |
| 0.1 | −87.8905 | 0.0 |
| 0.2 | 59.8194 | −17302.608 |
| 0.3 | 99.3994 | 4332.415 |
| 0.5 | 207.5322 | 0.0 |

In FIG. 8, since W is set equal to 3 in this example, the length of the time window used for the final rate calculation is larger than in the W equal to 1 case. For example, the sample with the initial rate of 0.30119 uses a time window of length 1.84. When W is set equal to 1, the time window length for a sample with an initial rate of 0.30119 is equal to 1.39.

Figure 10:
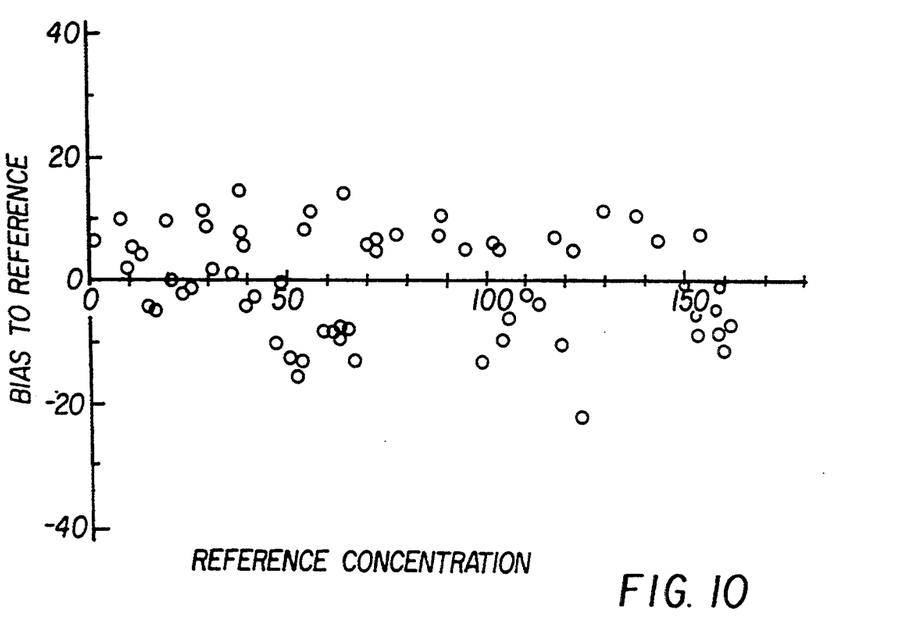
FIG. 10 is a plot of bias between predicted concentration and reference concentration of each sample, versus that reference concentration.

The bias between the predicted concentration and the reference concentration of each sample is plotted versus reference concentration in FIG. 10.

TABLE 9

| Reference Concen. | Initial Rate | Start of Window | End of Window | Final Rate | Predicted Concen. | Bias to Reference |
|---|---|---|---|---|---|---|
| 153.0 | 0.40389 | 0 | 0.8 | 0.40389 | 144.9 | −8.1 |
| 143.0 | 0.41277 | 0 | 0.8 | 0.41277 | 150.2 | 7.2 |
| 52.3 | 0.29051 | 0 | 1.89 | 0.17915 | 37.5 | −14.8 |

TABLE 9-continued

| Reference Concen. | Initial Rate | Start of Window | End of Window | Final Rate | Predicted Concen. | Bias to Reference |
|---|---|---|---|---|---|---|
| 28.6 | 0.29315 | 0 | 1.88 | 0.18148 | 40.4 | 11.8 |
| 63.7 | 0.30202 | 0 | 1.84 | 0.19643 | 56.5 | −7.2 |
| 149.5 | 0.41187 | 0 | 0.8 | 0.41187 | 149.6 | 0.1 |
| 58.7 | 0.30119 | 0 | 1.84 | 0.19089 | 50.9 | −7.8 |
| 159.5 | 0.41017 | 0 | 0.8 | 0.41017 | 148.6 | −10.9 |
| 35.7 | 0.28617 | 0 | 1.9 | 0.17888 | 37.2 | 1.5 |
| 98.7 | 0.33452 | 0 | 1.63 | 0.24512 | 86.1 | −12.6 |
| 64.3 | 0.32185 | 0 | 1.73 | 0.22764 | 78.9 | 14.6 |
| 121.5 | 0.39291 | 0 | 0.92 | 0.37116 | 127.0 | 5.5 |
| 105.5 | 0.36909 | 0 | 1.27 | 0.30285 | 100.1 | −5.4 |
| 117.0 | 0.38855 | 0 | 0.99 | 0.36629 | 124.6 | 7.6 |
| 16.2 | 0.25893 | 0 | 1.97 | 0.16012 | 12.0 | −4.2 |
| 7.5 | 0.26401 | 0 | 1.96 | 0.16428 | 17.9 | 10.4 |
| 41.4 | 0.30042 | 0 | 1.85 | 0.18072 | 39.5 | −1.9 |
| 63.1 | 0.2851 | 0 | 1.91 | 0.19448 | 54.6 | −8.5 |
| 88.7 | 0.36526 | 0 | 1.32 | 0.30278 | 100.1 | 11.4 |
| 48.3 | 0.30865 | 0 | 1.81 | 0.18868 | 48.6 | 0.3 |
| 157.5 | 0.41827 | 0 | 0.8 | 0.41827 | 153.5 | −4.0 |
| 63.8 | 0.30382 | 0 | 1.83 | 0.19454 | 54.7 | −9.1 |
| 61.4 | 0.30964 | 0 | 1.8 | 0.19344 | 53.5 | −7.9 |
| 123.5 | 0.37119 | 0 | 1.25 | 0.30924 | 101.9 | −21.6 |
| 66.4 | 0.28861 | 0 | 1.9 | 0.19375 | 53.9 | −12.5 |
| 70.1 | 0.31656 | 0 | 1.76 | 0.22299 | 76.4 | 6.3 |
| 38.0 | 0.30542 | 0 | 1.82 | 0.1868 | 46.5 | 8.5 |
| 159.0 | 0.42744 | 0 | 0.8 | 0.42744 | 159.2 | 0.2 |
| 46.8 | 0.29785 | 0 | 1.86 | 0.17887 | 37.2 | −9.6 |
| 88.0 | 0.36315 | 0 | 1.35 | 0.28479 | 95.9 | 7.9 |
| 0.6 | 0.2503 | 0 | 1.98 | 0.15702 | 7.4 | 6.8 |
| 50.3 | 0.2897 | 0 | 1.89 | 0.17979 | 38.3 | −12.0 |
| 77.1 | 0.33019 | 0 | 1.67 | 0.24175 | 85.0 | 7.9 |
| 19.4 | 0.28244 | 0 | 1.92 | 0.17297 | 29.7 | 10.3 |
| 14.8 | 0.26274 | 0 | 1.96 | 0.15956 | 11.2 | −3.6 |
| 30.9 | 0.28741 | 0 | 1.9 | 0.17585 | 33.4 | 2.5 |
| 94.7 | 0.36566 | 0 | 1.32 | 0.30393 | 100.4 | 5.7 |
| 152.5 | 0.40982 | 0 | 0.8 | 0.40982 | 148.4 | −4.1 |
| 29.6 | 0.29115 | 0 | 1.89 | 0.18031 | 39.0 | 9.4 |
| 37.8 | 0.30686 | 0 | 1.82 | 0.19281 | 52.9 | 15.1 |
| 129.5 | 0.39802 | 0 | 0.84 | 0.39802 | 141.5 | 12.0 |
| 20.7 | 0.27464 | 0 | 1.94 | 0.16669 | 21.3 | 0.6 |
| 54.1 | 0.29344 | 0 | 1.88 | 0.20368 | 63.0 | 8.9 |
| 55.5 | 0.30321 | 0 | 1.84 | 0.20897 | 67.2 | 11.7 |
| 161.0 | 0.41962 | 0 | 0.8 | 0.41962 | 154.3 | −6.7 |
| 52.0 | 0.29973 | 0 | 1.85 | 0.18001 | 38.6 | −13.4 |
| 153.5 | 0.41611 | 0 | 0.8 | 0.41611 | 152.2 | −1.3 |
| 9.6 | 0.25789 | 0 | 1.97 | 0.16015 | 12.0 | 2.4 |
| 99.9 | 0.36478 | 0 | 1.33 | 0.28675 | 96.4 | −3.5 |
| 53.5 | 0.30013 | 0 | 1.85 | 0.18184 | 40.8 | −12.7 |
| 104.0 | 0.35629 | 0 | 1.43 | 0.28021 | 95.0 | −9.0 |
| 11.1 | 0.26236 | 0 | 1.96 | 0.16366 | 17.1 | 6.0 |
| 48.5 | 0.29177 | 0 | 1.88 | 0.18934 | 49.3 | 0.8 |
| 23.5 | 0.28442 | 0 | 1.91 | 0.16737 | 22.2 | −1.3 |
| 25.4 | 0.28106 | 0 | 1.92 | 0.16933 | 24.9 | −0.5 |
| 72.4 | 0.33192 | 0 | 1.66 | 0.22829 | 79.2 | 6.8 |
| 137.5 | 0.4103 | 0 | 0.8 | 0.4103 | 148.7 | 11.2 |
| 72.2 | 0.31853 | 0 | 1.75 | 0.2248 | 77.4 | 5.2 |
| 65.1 | 0.30913 | 0 | 1.81 | 0.19762 | 57.6 | −7.5 |
| 113.0 | 0.37857 | 0 | 1.15 | 0.33256 | 109.8 | −3.2 |
| 39.3 | 0.28826 | 0 | 1.9 | 0.17766 | 35.7 | −3.6 |
| 110.0 | 0.37618 | 0 | 1.18 | 0.32866 | 108.3 | −1.7 |
| 103.5 | 0.37978 | 0 | 1.13 | 0.33095 | 109.2 | 5.7 |
| 38.4 | 0.30553 | 0 | 1.82 | 0.18522 | 44.7 | 6.3 |
| 154.0 | 0.43195 | 0 | 0.8 | 0.43195 | 162.1 | 8.1 |
| 118.5 | 0.37571 | 0 | 1.19 | 0.32997 | 108.8 | −9.7 |
| 158.5 | 0.41313 | 0 | 0.8 | 0.41313 | 150.4 | −8.1 |
| 102.0 | 0.37489 | 0 | 1.2 | 0.3293 | 108.5 | 6.5 |
| 13.0 | 0.26595 | 0 | 1.96 | 0.16424 | 17.9 | 4.9 |

The principle advantage of the invention is that it solves the consistent bias to reference problem encountered with the prior art SDW algorithm when applied to immuno-rate chemistries. The improvement results from determining the time window in the rate domain rather than the concentration domain.

Another advantage of the invention is that the time window is expressed in minutes rather than the number of density readings in the window. This seemingly minor detail allows the VET algorithm to function consistently across different analyzer types which have different internal timing templates. If this were not the case, then two analyzers types, with significantly different time intervals between density readings, would select different final time windows and, therefore, exhibit an analyzer type-to-type bias.

Other rate calculation methods can be used in determining the final rate, once the time window is determined. The method outlined in this disclosure is linear regression. An alternative method is to fit a linear combination of orthogonal polynomials to the kinetic data and then find the maximum rate of reaction. The latter rate determination technique is currently in use on the "Ektachem E700" ® analyzer of Eastman Kodak Company, using the first four well-known Chebyshev polynomials as the orthogonal polynomials.

The invention disclosed herein may be practiced in the absence of any element which is not specifically disclosed herein.

The invention has been described in detail with particular reference to certain preferred embodiments thereof, but it will be understood that variations and modifications can be effected within the spirit and scope of the invention.

What is claimed is:

1. A method of assaying in an analyzer analytes selected from the group consisting of digoxin, phenytoin, phenobarbital and CRP and having a change in optical density over time that is variable, the method being effective to minimize bias that occurs with said analytes, and comprising the steps of:

depositing the sample onto a dried slide test element,
detecting density readings over time,
making an initial rate reading comprising a rate of change of said density readings over time during an early time window,
comparing said initial rate reading with only known rates stored in said analyzer and selecting a time window from a plurality of time windows for final rate calculation based solely on the rate comparisons,
calculating a final rate from density readings within said selected time window,
and then calculating a concentration of said digoxin, phenytoin, phenobarbital or CRP from said final rate calculation,
whereby said window-selecting step is performed without first calculating a concentration, and a bias is avoided for said analytes that would occur if the window-selecting step were based upon a comparison with a predicted concentration.

2. A method of assaying in an analyzer, analytes selected from the group consisting of T4 and carbamazepine and having a change in optical density over time that is variable, the method being effective to minimize bias that occurs with said analytes, and comprising the steps of:

depositing the sample onto a dried slide test element,
detecting density readings over time,
making an initial rate reading comprising a rate of change of said density readings over time during an early time window,
comparing said initial rate reading with only known rates stored in said analyzer and selecting a time window from a plurality of time windows for final rate calculation based solely on the rate comparisons, calculating a final rate from density readings within said selected time window, and then calculating a concentration of said T4 or carbamazepine from said final rate calculation, whereby said window-selecting step is performed without first calculating a concentration, and a bias is avoided for said analytes that would occur if the window-selecting step were based upon a comparison with a predicted concentration.

3. A method of assaying in an analyzer, analytes selected from the group consisting of thyroid uptake, valproic acid, gentamicin, tobramycin, vancomicin, primidone, procainamide, N-acetyl procainamide, theophylline, Apo lipoproteins A and B, hCG, CKMB, troponin, myoglobin, IgE, IgM, and IgA and having a change in optical density over time that is variable, the method being effective to minimize bias that occurs with said analytes, and comprising the steps of:

depositing the sample onto a dried slide test element, detecting density readings over time, making an initial rate reading comprising a rate of change of said density readings over time during an early time window, comparing said initial rate reading with only known rates stored in said analyzer and selecting a time window from a plurality of time windows for final rate calculation based solely on the rate comparisons, calculating a final rate from density readings within said selected time window, and then calculating a concentration of said selected analyte from said final rate calculation, whereby said window-selecting step is performed without first calculating a concentration, and a bias is avoided for said analytes that would occur if the window-selecting step were based upon a comparison with a predicted concentration.

4. A method as defined in claims 1, 2 or 3, wherein said windows are expressed in said comparing step in minutes, instead of the number of readings within that window, so that final predicted concentrations are consistent between different types of analyzers.

5. A method as defined in claims 1, 2 or 3, wherein said calculating final rate includes calculating the rate from density readings over time using linear regression.

6. A method as defined in claims 1, 2 or 3, wherein said steps of comparing and selecting comprise the calculation of a final time window, FWL, using the equation $FWL = ML - [R^W \cdot (ML - NL)]$ wherein $ML =$ a predetermined maximum time window, in minutes, $NL =$ a predetermined minimum time window, in minutes, and R is determined from the equation $R = (InitRate - LowRate) \div (HighRate - LowRate)$ wherein InitRate = a rate of change in density over the time window from TIND to TIND+NL, HighRate and LowRate are predetermined high and low rates, respectively for said analyte assay, TIND is a predetermined induction time for said analyte, except that if $R > 1$, then $B = 1$, and for $R < 0$, $R = 0$.

* * * * *

UNITED STATES PATENT AND TRADEMARK OFFICE
CERTIFICATE OF CORRECTION

PATENT NO. : 5,449,624
DATED : September 12, 1995
INVENTOR(S) : Paul A. Kildal-Brandt, Thomas A. Weber It is certified that error appears in the above-indentified patent and that said Letters Patent is hereby corrected as shown below:

Column 12, line 25, after "tRate-LowRate)" delete "+" and insert --÷--.

Column 12, line 31, delete "B=1," and insert --
R=1,--.

Signed and Sealed this

Ninth Day of January, 1996

Attest:

BRUCE LEHMAN

Attesting Officer     Commissioner of Patents and Trademarks